(12) United States Patent
Najafi et al.

(10) Patent No.: US 9,005,141 B1
(45) Date of Patent: Apr. 14, 2015

(54) AMBULATORY SYSTEM FOR MEASURING AND MONITORING PHYSICAL ACTIVITY AND RISK OF FALLING AND FOR AUTOMATIC FALL DETECTION

(75) Inventors: Bijan Najafi, Highland Park, IL (US); Ashkan Vaziri, Brookline, MA (US); Ali-Reza Boloori, Ann Arbor, MI (US)

(73) Assignee: Biosensics, L.L.C., Cambridge, MA (US)

( * ) Notice: Subject to any disclaimer, the term of this patent is extended or adjusted under 35 U.S.C. 154(b) by 269 days.

(21) Appl. No.: 13/531,313

(22) Filed: Jun. 22, 2012

Related U.S. Application Data

(63) Continuation of application No. 12/249,948, filed on Oct. 12, 2008, now Pat. No. 8,206,325.

(60) Provisional application No. 60/979,557, filed on Oct. 12, 2007.

(51) Int. Cl.
*A61B 5/103* (2006.01)
*A61B 5/117* (2006.01)
(Continued)

(52) U.S. Cl.
CPC .............. *A61B 5/1117* (2013.01); *A61B 5/0004* (2013.01); *A61B 5/6823* (2013.01); *A61B 5/7203* (2013.01); *A61B 5/7225* (2013.01);
(Continued)

(58) Field of Classification Search
CPC ....... A61B 5/11; A61B 5/1116; A61B 5/1117
USPC ................................................. 600/587, 595
See application file for complete search history.

(56) References Cited

U.S. PATENT DOCUMENTS

| | | | |
|---|---|---|---|
| 3,702,999 | A | 11/1972 | Gradisar |
| 5,373,651 | A | 12/1994 | Wood |
| 5,396,227 | A | 3/1995 | Carroll et al. |

(Continued)

FOREIGN PATENT DOCUMENTS

| | | |
|---|---|---|
| EP | 1195139 A1 | 4/2002 |
| WO | WO 03/065891 A2 | 8/2003 |

OTHER PUBLICATIONS

Mathie et al., "Detection of daily physical activities using a triaxial accelerometer", Medical & Biological Engineering & Computing, 2003, vol. 41, pp. 296-301.*

(Continued)

*Primary Examiner* — Devin Henson
(74) *Attorney, Agent, or Firm* — Knobbe, Martens, Olson & Bear, LLP

(57) ABSTRACT

The present invention relates to a light-weight, small and portable ambulatory sensor for measuring and monitoring a person's physical activity. Based on these measurements and computations, the invented system quantifies the subject's physical activity, quantifies the subject's gait, determines his or her risk of falling, and automatically detects falls. The invention combines the features of portability, high autonomy, and real-time computational capacity. High autonomy is achieved by using only accelerometers, which have low power consumption rates as compared with gyroscope-based systems. Accelerometer measurements, however, contain significant amounts of noise, which must be removed before further analysis. The invention therefore uses novel time-frequency filters to denoise the measurements, and in conjunction with biomechanical models of human movement, perform the requisite computations, which may also be done in real time.

27 Claims, 8 Drawing Sheets

(51) Int. Cl.
*A61B 5/11* (2006.01)
*A61B 5/00* (2006.01)

(52) U.S. Cl.
CPC .................. *A61B 5/7282* (2013.01); *A61B 5/11* (2013.01); *A61B 5/1116* (2013.01)

(56) References Cited

U.S. PATENT DOCUMENTS

| | | | |
|---|---|---|---|
| 5,642,096 | A | 6/1997 | Leyerer et al. |
| 5,907,819 | A | 5/1999 | Johnson |
| 6,119,516 | A | 9/2000 | Hock |
| 6,201,476 | B1 | 3/2001 | Depeursinge et al. |
| 6,433,690 | B2 | 8/2002 | Petelenz et al. |
| 6,730,024 | B2 | 5/2004 | Freyre et al. |
| 6,890,285 | B2 | 5/2005 | Rahman et al. |
| 6,926,667 | B2 | 8/2005 | Khouri |
| 6,997,882 | B1 | 2/2006 | Parker et al. |
| 7,141,026 | B2 | 11/2006 | Aminian et al. |
| 7,166,063 | B2 | 1/2007 | Rahman et al. |
| 7,334,472 | B2 | 2/2008 | Seo et al. |
| 7,450,730 | B2 | 11/2008 | Berg et al. |
| 7,620,450 | B2 | 11/2009 | Kim et al. |
| 7,627,450 | B2 | 12/2009 | Lee et al. |
| 7,632,216 | B2 | 12/2009 | Rahman et al. |
| 7,634,379 | B2 | 12/2009 | Noble |
| 7,640,134 | B2 | 12/2009 | Park et al. |
| 7,701,354 | B2 | 4/2010 | Chung |
| 7,725,289 | B2 | 5/2010 | Nagashima et al. |
| 7,747,409 | B2 | 6/2010 | Ladetto et al. |
| 7,771,371 | B2 | 8/2010 | Avni |
| 7,857,771 | B2 | 12/2010 | Alwan et al. |
| 7,962,308 | B2 | 6/2011 | Makino |
| 7,983,872 | B2 | 7/2011 | Makino et al. |
| 8,007,450 | B2 | 8/2011 | Williams |
| 8,025,632 | B2 | 9/2011 | Einarsson |
| 8,109,890 | B2 | 2/2012 | Kamiar et al. |
| 8,206,325 | B1 | 6/2012 | Najafi et al. |
| 8,212,650 | B2 | 7/2012 | Tsern et al. |
| 8,242,879 | B2 | 8/2012 | Haynes et al. |
| 8,287,477 | B1 | 10/2012 | Herr et al. |
| 8,376,971 | B1 | 2/2013 | Herr et al. |
| 8,384,551 | B2 | 2/2013 | Ross et al. |
| 8,388,553 | B2 | 3/2013 | James et al. |
| 8,551,029 | B1 | 10/2013 | Herr et al. |
| 8,753,275 | B2 | 6/2014 | Najafi et al. |
| 2003/0065409 | A1 | 4/2003 | Raeth et al. |
| 2003/0139692 | A1* | 7/2003 | Barrey et al. ........... 600/595 |
| 2004/0015103 | A1* | 1/2004 | Aminian et al. ......... 600/595 |
| 2005/0043660 | A1 | 2/2005 | Stark et al. |
| 2005/0165336 | A1 | 7/2005 | Rahman et al. |
| 2006/0166157 | A1 | 7/2006 | Rahman et al. |
| 2006/0270949 | A1* | 11/2006 | Mathie et al. .......... 600/595 |
| 2007/0149359 | A1 | 6/2007 | Rahman et al. |
| 2007/0270214 | A1 | 11/2007 | Bentley |
| 2007/0293781 | A1 | 12/2007 | Sims et al. |
| 2008/0091762 | A1 | 4/2008 | Neuhauser et al. |
| 2008/0281555 | A1 | 11/2008 | Godin et al. |
| 2008/0281636 | A1 | 11/2008 | Jung et al. |
| 2008/0318683 | A1 | 12/2008 | Rofougaran et al. |
| 2009/0002152 | A1 | 1/2009 | Chung |
| 2009/0024065 | A1 | 1/2009 | Einarsson |
| 2009/0055223 | A1 | 2/2009 | Jung et al. |
| 2009/0058660 | A1 | 3/2009 | Torch |
| 2009/0069724 | A1 | 3/2009 | Otto et al. |
| 2009/0076345 | A1 | 3/2009 | Manicka et al. |
| 2009/0099495 | A1 | 4/2009 | Campos et al. |
| 2009/0192414 | A1 | 7/2009 | Yasuhara |
| 2009/0234249 | A1 | 9/2009 | Randolph |
| 2009/0292194 | A1 | 11/2009 | Libbus et al. |
| 2010/0121227 | A1 | 5/2010 | Stirling et al. |
| 2010/0286571 | A1 | 11/2010 | Allum et al. |
| 2010/0324455 | A1 | 12/2010 | Rangel et al. |
| 2011/0054359 | A1 | 3/2011 | Sazonov et al. |
| 2011/0115629 | A1 | 5/2011 | Holler et al. |
| 2012/0022667 | A1 | 1/2012 | Accinni et al. |
| 2012/0184878 | A1 | 7/2012 | Najafi et al. |
| 2013/0245785 | A1 | 9/2013 | Accini et al. |

OTHER PUBLICATIONS

U.S. Appl. No. 13/053,147, filed Mar. 21, 2011, Najafi et al., Unpublished.
U.S. Appl. No. 13/723,040, filed Dec. 20, 2012, Najafi et al., Unpublished.
American Diabetes Association, Apr. 7-8, 1999, Boston, Massachusetts, "Consensus development conference in diabetic foot wound care", Diabetes Care 22.8:1354 (Aug. 1999).
Armstrong et al., "Activity patterns of patients with diabetic foot ulceration", Diabetes Care, vol. 26(9):2595-2597 (2003).
Armstrong et al., "Continuous activity monitoring in persons a high rish for diabetes-related lower-extremity amputation", Journal of the American Podiatric Medical Association, vol. 91:451-455 (2001).
Armstrong et al., "Evaluation of removable and irremovable cast walkers in the healing of diabetic foot wounds: a randomized controlled trial", Diabetes Care, vol. 28:551-4 (2005).
Armstrong et al., "Variability in activity may precede diabetic foot ulceration", Diabetes Care, vol. 27(8):1980-1984 (2004).
Coleman et al., "The total contact cast, a therapy for plantar ulceration on insensitive feet", J.Am. Podiatr. Med. Assoc., vol. 74:548-552 (1984).
Helm et al., "Total contact casting in diabetic patients with neuropathic foot ulcerations", Arch. Phys. Med. Rehabil., vol. 65:691-693 (1984).
Lavery et al., "Reducing dynamic foot pressures in high-risk diabetic subjects with foot ulcerations", Diabetes Care, vol. 19(8):818-821 (1996).
Mizell, "Using gravity to estimate accelerometer orientation", Proceedings of the Seventh IEEE International Symposium on Wearable Computers, Computer Society (2003).
Najafi et al., "A novel ambulatory device for continuous 24-H monitoring of physical activity in daily life", North American Congress on Biomechanics (NACOB), Michigan, 2008.
Brand, Paul W. "The diabetic foot", Diabetes Mellitus, Theory and Practice, $3^{rd}$ Ed., Ellenberg M. Rifkin H., Ed. New York: Medical Examination Publishing, 1983, pp. 803-828.
Pecoraro et al., "Pathways to diabetic limb amputation", Diabetes Care, vol. 13(5):513-521 (1990).
Sinacore et al., "Diabetic plantar ulcers treated by total contact casting", Phys. Ther. vol. 67:1543-1547 (1987).
Walker et al., "Chronic diabetic neuropathic foot ulcerations and total contact casting: healing effectiveness and outcome predictability", Arch. Phys. Med. Rehabil., vol. 66:574 (1985).
Wu et al., "The pivotal role of offloading in the management of neuropathic foot ulceration", Curr. Diab. Rep. vol. 5:423-9 (2005).
Wu et al., "Use of pressure offloading devices in diabetic foot ulcers", Diabetes Care, vol. 31(11):2118-2119, (2008).
B. Najafi, K. Aminian, F. Loew, Y. Blanc, and P. A. Robert, "Measurement of standsit and sit-stand transitions using a miniature gyroscope and its application in fall risk evaluation in the elderly," *Ieee Transactions on Biomedical Engineering*, vol. 49, pp. 843-851, 2002.
B. Najafi, K. Aminian, A. Paraschiv-Ionescu, F. Loew, C. J. Bula, and P. Robert, "Ambulatory system for human motion analysis using a kinematic sensor: Monitoring of daily physical activity in the elderly," *Ieee Transactions on Biomedical Engineering*, vol. 50, pp. 711-723, 2003.
R. W. Bohannon, A. W. Andrews, and M. W. Thomas, "Walking speed: reference values and correlates for older adults," *J Orthop Sports Phys Ther*, vol. 24, pp. 86-90, 1996.
K. Aminian, B. Najafi, C. Bula, P. F. Leyvraz, and P. Robert, "Spatio-temporal parameters of gait measured by an ambulatory system using miniature gyroscopes," *Journal of Biomechanics*, vol. 35, pp. 689-699, 2002.
K. Aminian, K. Rezakhanlou, E. De Andres, C. Fritsch, P. F. Leyvraz, and P. Robert, "Temporal feature estimation during walking using miniature accelerometers: an analysis of gait improvement after hip arthroplasty," *Medical & Biological Engineering & Computing*, vol. 37, pp. 686-691, 1999.

(56) References Cited

OTHER PUBLICATIONS

S. R. Cummings, M. C. Nevitt, and S. Kidd, "Forgetting falls. The limited accuracy of recall of falls in the elderly," *J Am Geriatr Soc*, vol. 36, pp. 613-616, 1988.

D. Oliver, M. Britton, P. Seed, F. C. Martin, and A. H. Hopper, "Development and evaluation of evidence based risk assessment tool (STRATIFY) to predict which elderly inpatients will fall: case-control and cohort studies," *Bmj*, vol. 315, pp. 1049-1053, 1997.

M. E. Tinetti, T. F. Williams, and R. Mayewski, "Fall risk index for elderly patients based on number of chronic disabilities," *Am J Med*, vol. 80, pp. 429-434, 1986.

K. Doughty, R. Lewis, and A. McIntosh, "The design of a practical and reliable fall detector for community and institutional telecare," *J Telemed Telecare*, vol. 6 Suppl 1, pp. S150-154, 2000.

U. Lindemann, A. Hock, M. Stuber, W. Keck, and C. Becker, "Evaluation of a fall detector based on accelerometers: a pilot study," *Med Biol Eng Comput*, vol. 43, pp. 548-551, 2005.

N. Noury, G. Barralon, G. Virone, P. Boissy, M. Hamel, and P. Rumeau, "A smart sensor based on rules and its evaluation in daily routines," presented at 25th Annual International Conference of the IEEE Eng. Med. Biol. Society, 2003.

\* cited by examiner

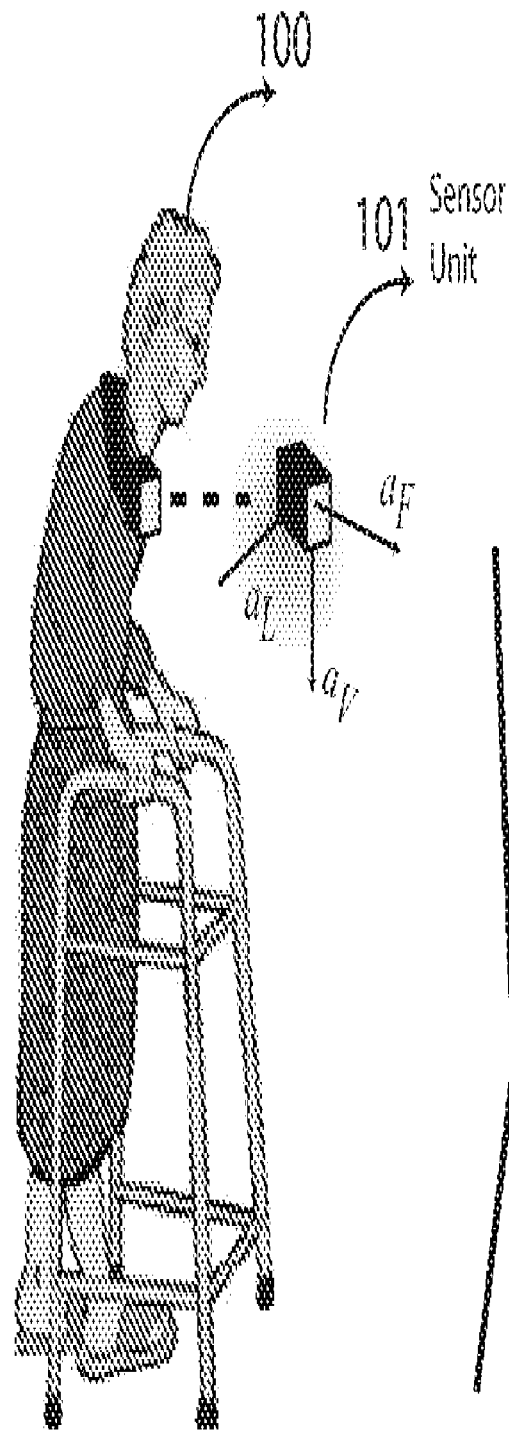
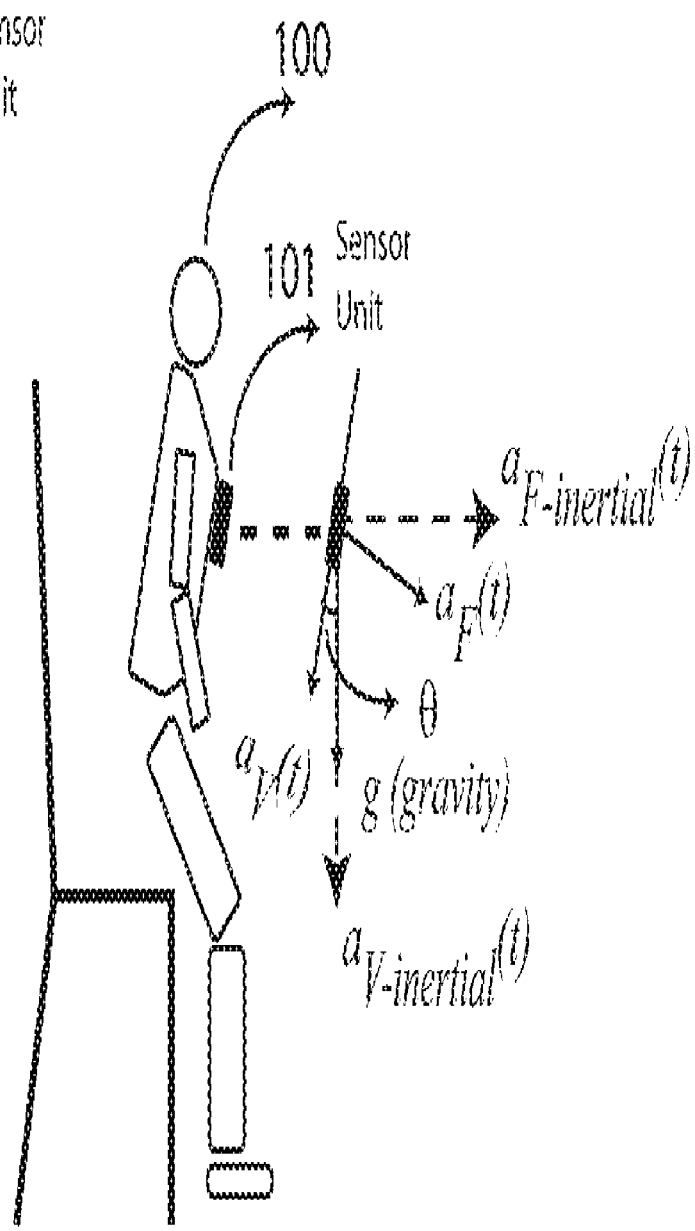
FIG. 1a
FIG. 1b

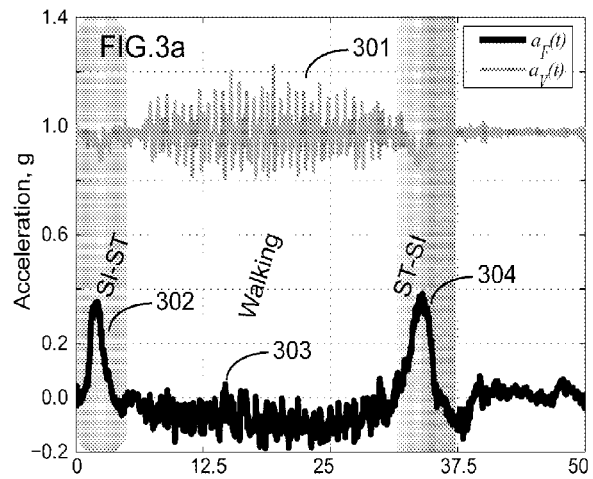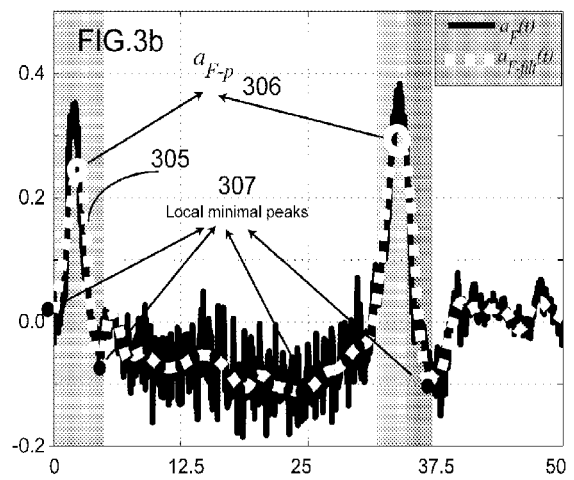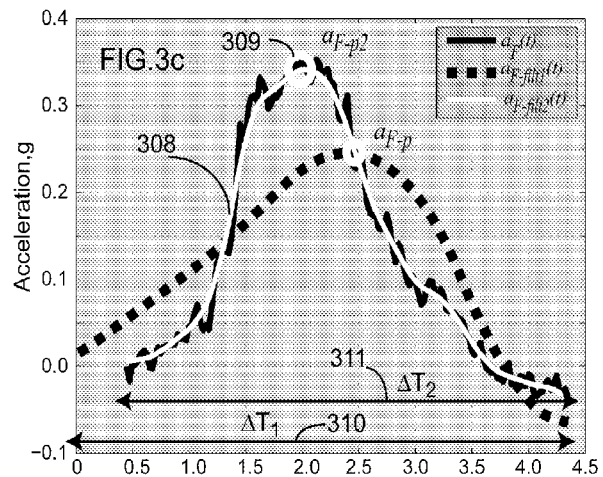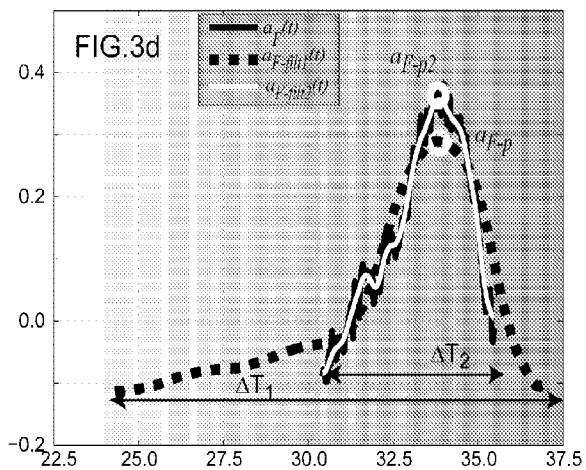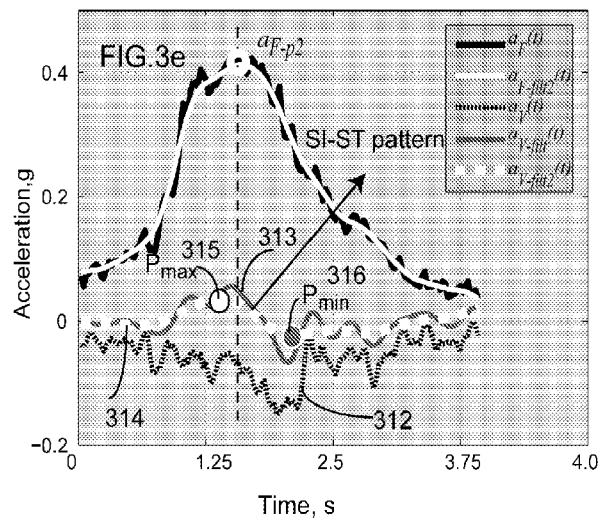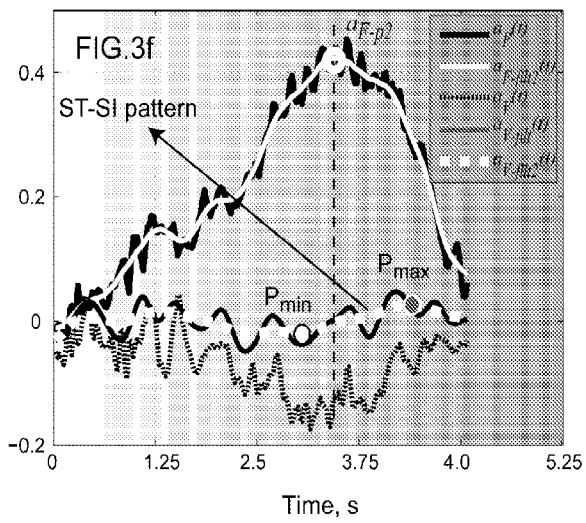

AMBULATORY SYSTEM FOR MEASURING AND MONITORING PHYSICAL ACTIVITY AND RISK OF FALLING AND FOR AUTOMATIC FALL DETECTION

CROSS-REFERENCE TO RELATED APPLICATIONS

This application is a continuation of U.S. patent application Ser. No. 12/249,948, filed Oct. 12, 2008, which claims the benefit of U.S. Provisional Application No. 60/979,557, filed Oct. 12, 2007, each of which is incorporated herein in its entirety by reference.

FIELD

This invention generally relates to body movement monitoring systems, specifically to an ambulatory system which (1) measures and quantifies parameters related to the user's postures and movements; (2) evaluates the user's risk of falling; and (3) automatically detects the user's falls.

BACKGROUND OF THE INVENTION

We envision several uses for the present invention. In the fields of elderly care and physical therapy, the present invention finds several important uses. We envision that the invented system can provide both qualitative and quantitative monitoring of an elderly person's physical activity (PA) during his or her everyday life. This information is useful for several reasons: first, PA monitoring can accurately determine the user's state of physical and mental health, identifying subacute changes in their health status. For example, this system can detect early deteriorations in the amount and quality of the subjects' PA due to various health conditions (e.g., congestive heart failure, development of infections, etc.) Second, PA monitoring provides valuable information about the sequence of the elderly person's movements during the time window surrounding their falls. This information significantly aids the development of alert systems to predict, and ideally, prevent fall occurrences. Third, assessment of the effects of new drugs and pain treatments are significantly advanced through monitoring of the subjects' physical activity during his or her everyday life. Fourth, monitoring of PA in the elderly population can, over time, provide insight into qualitative and quantitative changes in PA as a result of all adverse physical events, such as functional declines or hospitalizations. Persons at risk can therefore be identified, and novel preventive interventional methods may be tailored to their needs. The invented system also finds use in remote monitoring and telecare of people suffering from various diseases, such as Alzheimer's, as well as of those recovering and rehabilitating from diseases and medical procedures.

In clinical research and studies, the invented system provides valuable insight into the mechanisms and factors influencing physical activity and balance by quantifying the subject's PA and risk of falling (RoF) in all contexts, including everyday life.

In drug development, the invented system can be used to study the role of various drugs and treatment procedures on the physical activity and RoF of people during clinical studies.

In athletics training, this system provides valuable feedback on the user's body movements, and can be a valuable tool for both training and on-field performance measurement.

Measurement and monitoring of PA by the present invented system also finds use in weight management by providing intelligent feedback to the user about his or her daily energy expenditures.

Postural Transitions:

Najafi et al. [1-3] have developed algorithms for identifying postural transitions (PT), e.g., sit-to-stand (SI-ST) and stand-to-sit (ST-SI) from data recorded by a gyroscopic sensor attached to the subject's trunk. The high power-consumption rates of gyroscopes, however, severely limits the applicability of these algorithms for applications outside of the laboratory (which include everyday life applications), since such a system has an autonomy of only a few hours, therefore requiring frequent recharging or exchanges of the battery. Although the addition of more batteries would increase the device's autonomy, it will also increase its size and weight, thus hindering the subject's natural movements.

By contrast, the algorithms developed as part of the present invention use accelerometer data in place of gyroscope data, and therefore enable long-term, autonomous operability of the system.

Gait Analysis:

Proper gait function (i.e., quality of gait) requires the ability to maintain safe gait while navigating in complex and changing environments, and to conform one's gait to different task demands. Furthermore, a person's quality of gait is closely linked to his or her overall state of health. For example, walking speed correlates with the individual's ability to live independently, with the ability to perform various activities of daily life (such as safely crossing a traffic intersection), and with reductions in the risk of falling [4].

Since evaluation of a person's overall health and quality of life are greatly facilitated by knowledge of his or her gait function during everyday life, a system that can automatically extract gait-related parameters with minimal hindrance of the user's movements is highly useful. To date, however, fully satisfactory methods and systems have not been developed. Current techniques for computing a person's gait parameters are primarily based on the use of vertical accelerometer signals, together with a peak-detection algorithm to identify the walking step. Such techniques, however, possess several important shortcomings.

First, they cannot remove the rotational artifacts generated by the body segment to which the sensor has been attached. These noise artifacts stem from the gravitational component of the accelerometer signal. While they can be easily removed in the case of healthy young subjects, such artifacts pose a key challenge to accurate computation of gait parameters in the case of patients and the elderly—who tend to walk slowly and may use walking aids. Second, current algorithms cannot discriminate between acceleration peaks associated with postural transitions, and those due to walking steps, thus leading to very low specificity during activity daily life (ADL).

Alternative technologies for estimating the gait pattern use combinations of gyroscopes and/or accelerometers attached to the lower limbs [5-7]. Use of gyroscopes decreases the autonomy of the system due to high power consumption. Moreover, attaching the sensors on lower limbs hinders the user's movements, who must carry the system during ADL.

The present invention accurately identifies the user's walking periods during ADL, discriminates between left and right gait steps, and estimates the spatiotemporal parameters of gait (e.g., swing, stance, double support, and gait speed) using only accelerometers. Aminian et al. (1999) [7] have suggested an algorithm, based on a neural network, that extracts spatiotemporal parameters of gait using accelerometers attached to the subject's lower back. This algorithm, however, requires a calibration/pre-learning stage that can only be accomplished by having subjects walk within a constrained space of a gait lab. This requirement renders that algorithm impractical for use during everyday life activities. By contrast, the algorithms developed as part of the present invention require no initial calibrations, and therefore can be easily used by any individual.

In so doing, our algorithms overcome the shortcomings present in the prior art: the small, lightweight and portable sensory module, attached to the subject's chest, poses minimal hindrance to his or her movements during ADL. Furthermore, the accelerometers consume considerably less power than do gyroscopes, leading to significantly longer operational times. Moreover, the invented system provides significantly higher accuracy in discriminations, and better removes rotational noise artifacts.

Risk of Falling:

Evaluation of the individual's risk of falling is required in providing adapted assistance and preventive measures for subjects deemed at a high risk of falling. This risk is generally evaluated by using questionnaires, which have shortcomings such as subjectivity and limited accuracy in recall [8]. Risk of falling can also be evaluated by clinical and functional tests, such as assessments of posture and gait, independence in daily life, cognition, and vision [9-10]. However, an objective method for remotely monitoring this risk through the monitoring the daily physical activity (PA) has not yet been developed. By contrast, the present invention assesses and monitors the user's risk of falling through monitoring and measurement of his or her daily physical activity.

Automatic Fall Detection:

Of the health problems commonly associated with aging, the most serious is falling—defined as a person's trunk, knee, or hand unintentionally coming to rest on the ground or a lower level below the waist. A reliable system to remotely detect falls allows delivery of early care to these persons, and decreases the detrimental consequences of falls, leading to substantial health-care cost savings. Current fall alarm systems require activation and are therefore inappropriate in falls due to syncope, a loss of consciousness associated with cerebro-vascular accidents. Moreover, persons suffering from Alzheimer's disease—affecting approximately one-third of persons aged 80 years and older—may not be capable of activating such systems. A reliable system capable of sending automatic alarms when assistance is necessary will therefore provide an innovative way to support these patients and their caregivers. Automatic fall reporting would also be important in clinical research to reliably record occurrence of falls.

Current detection of falls essentially relies on self-reporting and complex reporting systems with daily phone-call reminders. In fact, for the research community interested in fall prevention, the documentation of falls is a methodological pitfall, and no unanimously accepted method for reporting falls exists. Little data support claims to the reliability and validity of different reporting systems. Oral reports have many limitations due to the cognitive status of the subjects as well as mental factors such as shame or fear of reporting. Finally, fall events associated with loss of consciousness due to syncope, stroke or epileptic seizures are not always recognized.

While a number of different approaches to fall detection have appeared in recent years [11-14], they have primarily used patterns recorded by tri-axial accelerometers to identify shocks related to falls, independent of the previous posture (i.e. sitting, lying, standing) and/or the state of activity (e.g. rest, walking, turning, postural transition, etc) of the faller. Not using the key information about the person's previous posture and state of activity likely gives rise to false detections, dramatically decreasing the accuracy of the fall detector. The present invention, by contrast, identifies falls with high sensitivity and specificity using only signals from accelerometers.

SUMMARY

The present invention consists of a body movement monitoring system that includes a sensing unit, attachable to the upper part of the user's body, such as trunk or shoulder, comprising a tri-axial accelerometer, or, three mono-axial accelerometers measuring accelerations in three perpendicular directions. The system also includes one or more processor circuits configured to: process the signals recorded by the accelerometer(s) and derive information related to the subject's movement from said accelerometer(s). Some or all of these analyses may be carried out on-board the sensing unit. In all cases, software-based algorithms, developed as part of the present invention, are integrated with the processor circuits performing the analyses. One or more data storage systems are also included in the system, and are configured to store signals recorded by said accelerometer(s), or the information derived by one of said processor circuits, or both. One or more of said data storage systems may be housed within said sensor. An optional communications system, configured to transmit at least a portion of the data recorded by said accelerometers, or at least a portion of the information derived by said the processor circuit housed within the sensor, or both, may also be housed with the sensor. The information derived from the measured acceleration signals are used to monitor and quantify the user's physical activity; automatically detect the user's risk of falling; and assess the user's risk of falling. The required computations are performed according to software-based algorithms, developed as part of the present invention, which use at least one biomechanical model of human body movement, and one or more signal processing time-frequency filters.

BRIEF DESCRIPTION OF THE DRAWINGS

The foregoing and other objects, features, and advantages of the invention will be apparent from the following detailed description of the invention, as illustrated in the accompanying drawings, in which like reference numerals designate like parts throughout the figures thereof and wherein:

FIG. 1a illustrates how an elderly subject may wear the sensory module, and also shows the three components of acceleration measured by the sensory unit;

FIG. 1b is a two-dimensional schematic of a subject wearing the sensory unit, and shows the subject's trunk lean angle θ, the direction of gravity, as well as the frontal and vertical acceleration components;

FIG. 3 demonstrates the operation of the algorithms in determining the time, type and duration of the subject's postural transitions;

DETAILED DESCRIPTION OF EXEMPLARY EMBODIMENTS

Figure 2:
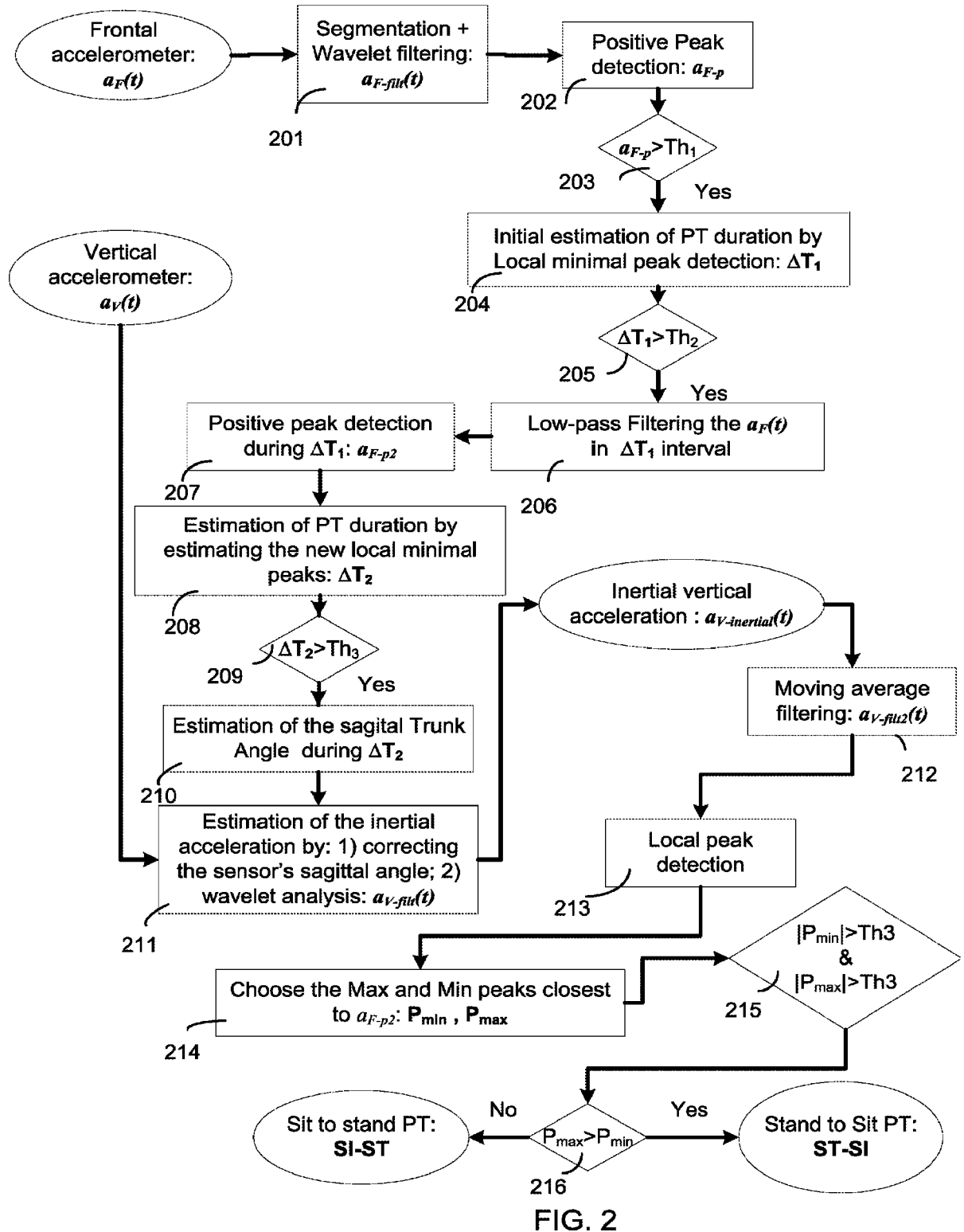
FIG. 2 is a flowchart of the algorithms used to determine the time, time and duration of the subject's postural transitions.

The present invention consists of a system and method for performing the following tasks during the user's everyday life: (1) monitoring the user's physical activity; (2) automatically detecting the user's falls; and (3) assessing the user's risk of falling. The second and third tasks are based on the results obtained from the first.

As shown by FIG. 1a, the system includes a sensing module ("SM") 101 for sensing, filtering and analyzing the user's 100 body movements. The SM 101 is positioned on the user's 100 upper body (typically, on the user's chest or torso), and is comprised of one to three accelerometers, each of which may be mono-axial or multi-axial. The only constraints on the accelerometer configuration are that (1) accelerations in three perpendicular directions must be measured; and (2) the accelerometer(s) is(are) configured to record accelerations in the frontal (F), vertical (V) and lateral (L) directions, which directions are relative to the user 100 (see FIG. 1a). In this document, all acceleration quantities are expressed in units of g (i.e., as multiples or fractions of g), where g is the gravitational constant equaling 9.81 m/s$^2$: for example, by this convention an acceleration magnitude of 9.81 m/s$^2$ (in SI units) will be expressed 1.

The SM 101 may also include a data-storage system for storing the measured accelerations. An optional on-board communications system provides the SM 101 the capability to transmit the collected data and/or analyzed signals through either wired or wireless links for storage and/or for further offline analysis.

Analysis of the measured acceleration signals may be carried out (1) entirely on-board the SM 101, (2) partially on-board the SM 101 and partially at other location(s), or (3) entirely at other location(s). In case some or all of the analysis is (are) carried out on-board the SM 101, a data processing circuit will be included on-board the SM to carry out the required computations according to software-based algorithms developed as part of the present invention. In case some or all of the analysis is carried at location(s) separate from the SM 101, the required data processing circuits performing the analysis may be ordinary or special-purpose computers, and are integrated with software-based algorithms developed as part of the present invention.

A. Monitoring the User's Physical Activity

Monitoring the user's physical activity consists of monitoring and assessing the user's postures, movements, trunk tilt, as well as fall-related task parameters. To this end, the system computes various parameters associated with the subject's movement from the data recorded by the SM 101. These parameters consist of: (a) the subject's trunk tilt (specified in degree, measuring the angle between the subject's trunk axis, and the axis aligned with the gravitational force—see FIG. 1b); (b) the type of the subject's postural transitions (PT); (c) the time of the subject's postural transitions; (d) the duration of the subject's postural transitions; (e) the duration of the subject's locomotion; (f) characterization of the subject's locomotion (gait analysis); and (g) the type of subject's postures (e.g., sitting, standing, lying).

Use of accelerometers in place of gyroscopes by the present invention allows for long-term autonomous operability of the system. The associated challenges introduced by this replacement, however, consist of processing the resulting noisy accelerometer signals during everyday living activities.

I. Identifying the Types of Postural Transitions, and Computing their Durations and Occurrences:

The flowchart in FIG. 2 and FIGS. 3a-3f demonstrate the operation of the algorithms, developed as part of the present invention, used to continuously determine the type, time, and duration of the subject's postural transitions (in this case, SI-ST and ST-SI) during everyday movements. The algorithms use the frontal and vertical accelerometer signals—$a_F(t)$ and $a_V(t)$ respectively in FIG. 1a—where their time-varying nature is explicitly shown by including the time variable t in the notation used for these signals. In implementing the algorithms, the time variable t is by necessity discrete.

FIG. 3a shows an example of the acceleration patterns recorded by the vertical and frontal accelerometers from an elderly subject with a high risk of falling ($a_V(t)$: gray line 301; $a_F(t)$: black line). As identified on the plot, the pattern consists of a sit-to-stand (SI-ST) postural transition followed by a period of walking and turning, followed by another postural transition (stand-to-sit; ST-SI).

As shown in FIG. 2, the algorithm performs the following steps on the frontal accelerometer signal to determine the occurrence, duration and type of the postural transitions:

1) segmenting, followed by wavelet filtering (box 201 in FIG. 2) to remove signal artifacts induced by locomotion (e.g., walking, climbing or descending the stairs, etc.)—see also the white trace 305 in FIG. 3b, an example of the resulting filtered signal $a_{F\text{-}filt}(t)$;
2) locating the local maximum peaks (denoted by $a_{F\text{-}p}$ 306 in FIG. 3b) in the filtered signal $a_{F\text{-}filt}(t)$ 305 through a peak-detection algorithm—this step corresponds to box 202 in FIG. 2;
3) for each postural transition, corresponding to a particular $a_{F\text{-}p}$ 306, computing an initial estimate of the postural transition duration ($\Delta T_1$) by (boxes 203 and 204):
   (i) determining whether $a_{F\text{-}p}$ 306 is greater than a pre-defined threshold Th1;
   (ii) if yes, locating the local minima 307 in $a_{F\text{-}filt}(t)$ 305, within a specified time window, that precede and follow the particular maximum peak $a_{F\text{-}p}$ 306 see FIG. 3b;
   (iii) computing $\Delta T_1$ 310 as the duration of the resulting time interval $I_1$ separating the local minima computed above.

The above steps suppress and remove signal artifacts, such as noisy peaks, associated with shocks or other locomotion activities.

Following the initial determination of the postural transition duration ($\Delta T_1$), the system computes a more accurate estimate of the postural transition duration, $\Delta T_2$, by applying additional filters to the frontal acceleration signal only within a time interval that is centered at $I_1$, but that is typically 10% to 30% longer in duration than $\Delta T_1$ 310. Such filtering of the frontal acceleration signal significantly decreases the requisite calculation costs, therefore enabling real-time implementation of the algorithm.

If the value $\Delta T1$ 310 surpasses a defined threshold, $Th_2$ (box 205 in FIG. 2), the following steps are performed on the frontal accelerometer signal $a_F(t)$ only during a time interval that is centered at $I_1$ but that is typically 10% to 30% longer in duration:

1) as represented by box 206 in FIG. 2, low-pass filtering the aF(t) signal during the time interval $I_1$ by a wavelet;

2) as represented by box 207 in FIG. 2, locating the maximum peak ($a_{F-p2}$ 309) in the resulting filtered signal $a_{F-filt2}(t)$ 308 during time interval $I_1$ (see FIG. 3c);

3) within a specified time window, locating a local minimum in $a_{F-filt2}(t)$ closest to, and preceding, the particular maximum peak $a_{F-p2}$ (box 207 in FIG. 2);

4) within a specified time window, locating a local minimum in $a_{F-filt2}(t)$ closest to, and following the same maximum peak (box 207 in FIG. 2);

5) computing $\Delta T_2$ 311 (see FIG. 3c) as the duration of the resulting time interval $I_2$ separating the local minima computed above (box 207 in FIG. 2);

The time of the maximum peak $a_{F-p2}$ represents the time of the postural transition, and the parameter $\Delta T_2$ 311 represents the estimate of the duration of the postural transition.

For each postural transition, following the computation of its time of occurrence and its duration, the system uses the step-by-step algorithm below to identify its type (e.g., ST-SI or ST-SI):

1) as represented by boxes 209 and 210 in FIG. 2, for each postural transition if $\Delta T_2$ exceeds a predefined threshold $Th_3$, estimate the trunk tilt angle in the sagittal plane, θ, using a low-pass filtering of the $a_F(t)$ signal during the corresponding time interval $I_2$—since $a_F(t)$ consists of a θ-dependent gravitational component as well as a higher frequency, pure frontal-acceleration component, low-pass filtering removes the pure frontal-acceleration component, leading to a quantity proportional to the $\sin(\theta)$;

2) estimate the time-varying inertial frontal and vertical accelerations $a_{F-interial}(t)$ and $a_{V-interial}(t)$ through the following coordinate transformation (see box 211 in FIG. 2):

$$\begin{bmatrix} a_{F-inertial}(t) \\ a_{V-inertial}(t) \end{bmatrix} = \begin{bmatrix} \cos(\theta(t)) & -\sin(\theta(t)) \\ \sin(\theta(t)) & -\cos(\theta(t)) \end{bmatrix} \begin{bmatrix} a_F(t) \\ a_V(t) \end{bmatrix} + \begin{bmatrix} 0 \\ 1 \end{bmatrix},$$

where, as mentioned before, the acceleration signal is expressed in units of g (g represents the gravitational constant (9.81 m/s²))—see also FIG. 1b for a free-body diagram showing the inertial acceleration components;

3) in parallel, apply an adequate, cascaded low-pass filter to remove the artifacts from $a_V(t)$, where the low-pass filter functions as follows:

(i) removal of the gravitational component of $a_V(t)$ 312 (FIG. 3e) using the following equations (see also box 211 in FIG. 2):

$$a_F(t) = [a_{V-inertial}(t) + 1]\sin(\theta(t)) + a_{F-inertial}(t)\cos(\theta(t));$$

$$a_V(t) = [a_{V-inertial}(t) + 1]\cos(\theta(t)) + a_{F-inertial}(t)\sin(\theta(t));$$

$$a_{V-filt}(t) = \sqrt{[a_F(t)]^2 + [a_V(t)]^2};$$

(ii) low-pass filtering the resulting signal $a_{V-filt}(t)$ 313, leading to $a_{V-filt2}(t)$; and (iii) filtering this signal by a moving-average filter to obtain $a_{V-filt}3(t)$ (see also box 212 in FIG. 2);

4) as exemplified in FIGS. 3e-3f, determine the local peaks in $a_{V-filt3}(t)$ using a peak detection algorithm (box 213 in FIG. 2); the resulting positive and negative peaks—$P_{max}$ 315 and $P_{min}$ 316, respectively—exceeding a predefined threshold $Th_4$, are identified (boxes 214 and 215 in FIG. 2);

5) classify the detected postural transition as sit-to-stand or stand-to-sit through the sequence by which $P_{max}$ and $P_{min}$ occur: e.g., a $P_{max}$ followed by a $P_{min}$ identifies the postural transition as a sit-to-stand pattern (box 316 in FIG. 2; see also FIGS. 3e-3f);

6) apply a post-processing algorithm to prevent misclassification of postures and postural transitions: for each postural transition, the classification as ST-SI or SI-ST will be corrected based on the preceding and subsequent sequences of postural transitions.

Figure 4:
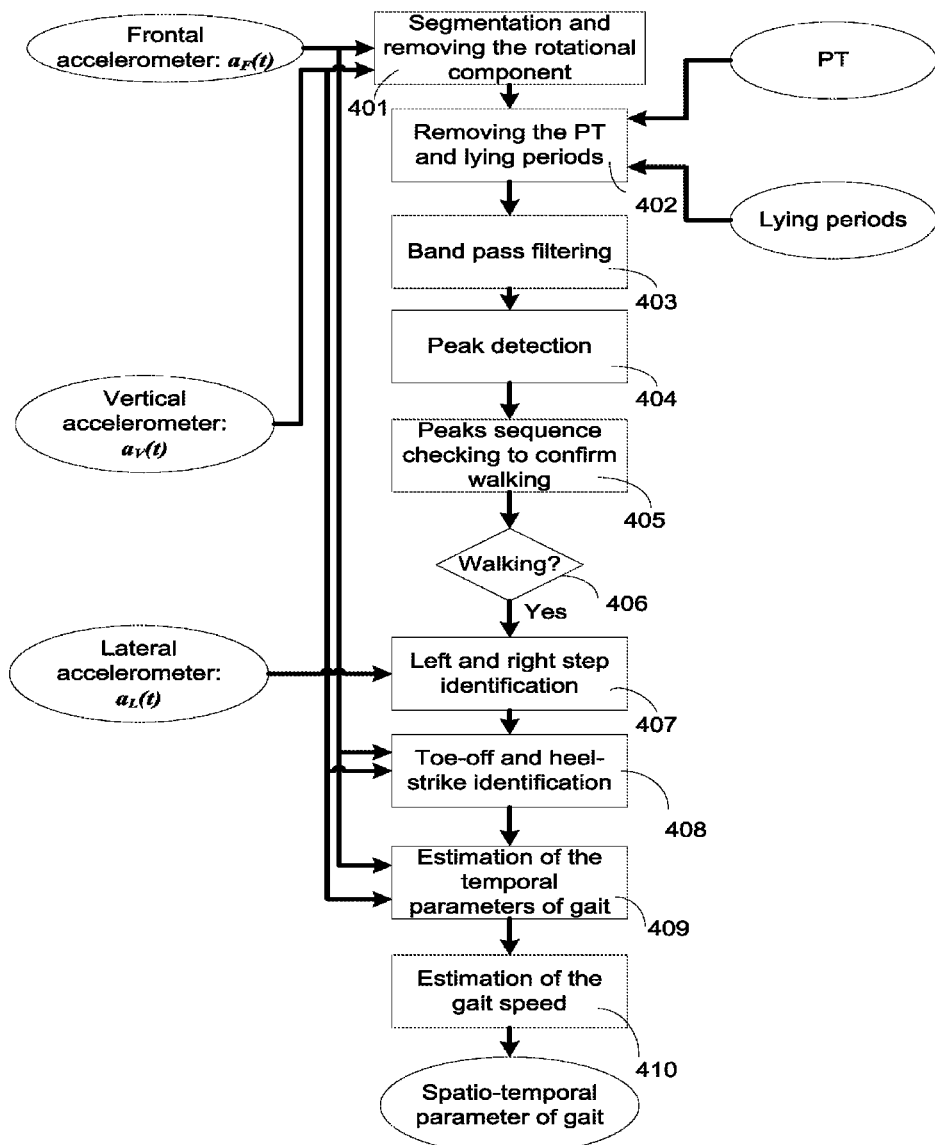
FIG. 4 is a flowchart of the algorithms used to identify the walking periods, and to compute the subject's spatiotemporal parameters of gait.

II. Analyzing Gait, and Identifying the Corresponding Walking Periods:

FIG. 4 describes in flowchart form the software-based algorithm, developed as part of the invented system, to identify the subject's walking periods and measure his or her gait parameters. Using data recorded by the accelerometers, the algorithm can distinguish left and right gait steps, as well estimate the spatiotemporal gait parameters, e.g., swing, stance, double support, and gait speed.

Figure 5:
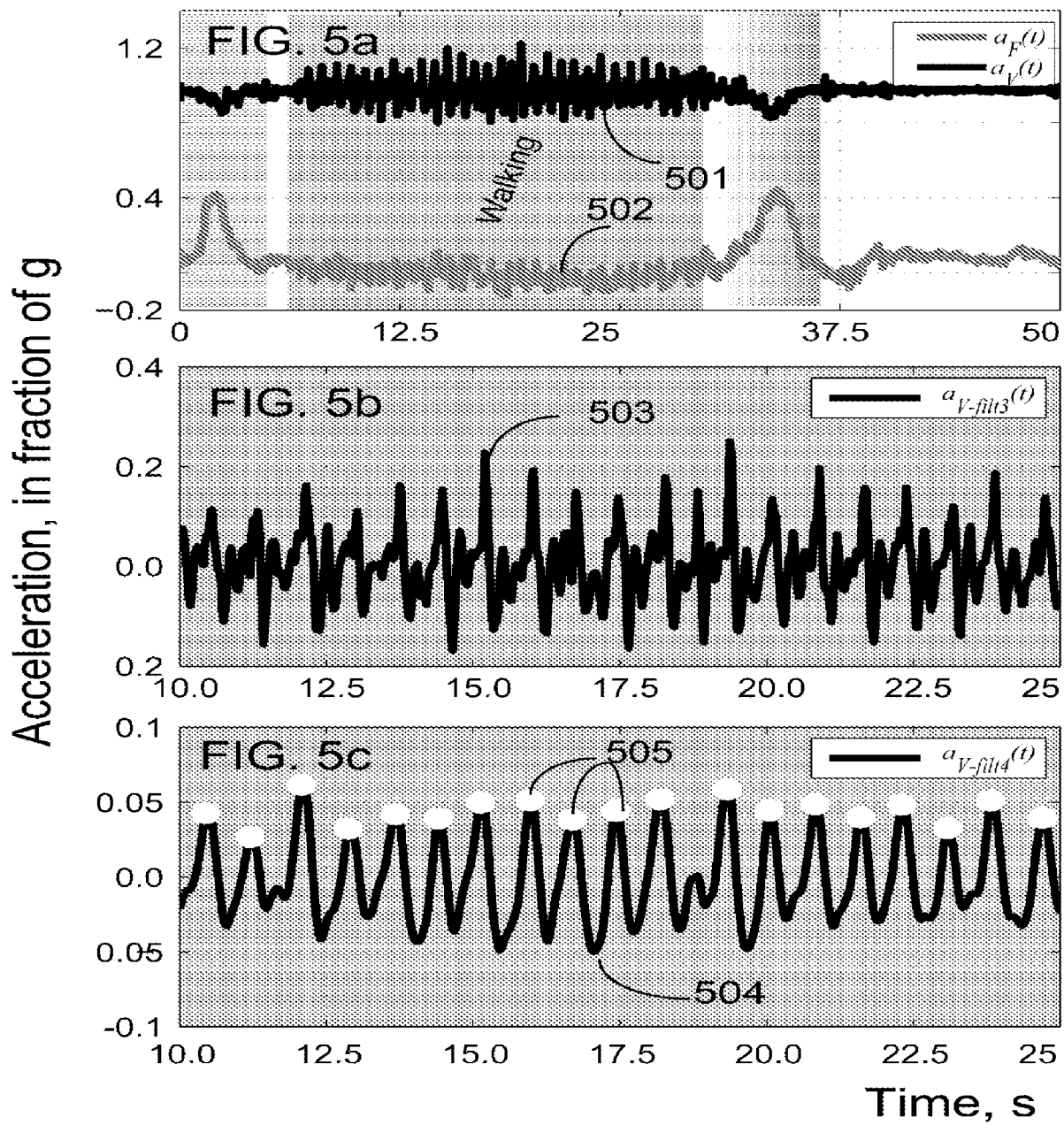
FIG. 5 demonstrates the operation of the algorithms in identifying the walking periods, and in computing the subject's spatio-temporal parameters of gait.

The algorithm consists of the following steps:

1) remove from consideration data during time periods associated with postural transitions and lying (boxes 401-402 in FIG. 4);

2) compute the time-varying norm (i.e., time-varying magnitude) of the vertical and horizontal accelerometer signals as:

$$a_F(t) = [a_{V-inertial}(t) + 1]\sin(\theta(t)) + a_{F-inertial}(t)\cos(\theta(t));$$

$$a_V(t) = [a_{V-inertial}(t) + 1]\cos(\theta(t)) + a_{F-inertial}(t)\sin(\theta(t));$$

$$a_{V-filt}(t) = \sqrt{[a_F(t)]^2 + [a_V(t)]^2};$$

where θ(t) represents the time-varying trunk angle, and $a_{V-inertial}(t)$ and $a_{F-inertia}(t)$ represent the time-varying vertical and frontal acceleration components, respectively; FIG. 5b shows the resulting waveform, $a_{V-filt3}(t)$ 503—see FIG. 1b for the free-body diagram leading to the above formulas; these formulas allow for suppression of the movement artifacts derived from the rotations of the subject's trunk;

3) remove the gravitational component from the vertical acceleration signal in two steps: first, use formula stated in step (2) to compute aV-filt3(t) 503; second, as shown by box 403 in FIG. 4, band-pass filter the result, leading to $a_{V-filt4}(t)$ 504 (see FIG. 5c);

4) as represented by box 404 in FIG. 4, identify gait steps as the peaks 505 (see, FIG. 5c) in the $a_{V-filt4}(t)$ signal 504;

5) verify the sequence of the detected peaks according to pre-defined conditions for gait patterns (box 405 in FIG. 4);

6) distinguish left and right steps (box 407 in FIG. 4) using the signal $a_L(t)$ from the lateral accelerometer—specifically, (i) the subject's lateral velocity $v_L(t)$ is computed by integrating $a_L(t)$ during the recognized walking periods; (ii) the relationship between the locations of the positive and negative peaks in $v_L(t)$ with the identified peak in the filtered vertical acceleration signal, $a_{V-filt4}(t)$ 504, allows for left and right steps be distinguished.

This algorithm, furthermore, enables both the recognition of undetected gait steps, and the removal of false detected steps.

The system, through another algorithm, computes the times of heel-strike (initial contact) and toe-off (final contact) events using information extracted from the frontal and vertical acceleration signals—this step corresponds to box 408 in FIG. 4. Specifically, the local minimum and maximum peaks in the frontal acceleration signal surrounding each identified vertical acceleration peak are used to identify heel-strike event and toe-off events. Following a heel-strike event, the subject's trunk continues to moves forward. As the toe-off event occurs, the trunk slows down, leading to a negative peak in the frontal accelerometer signal. Although a heel-strike event can be estimated using the vertical acceleration signal, when an impact is identified, the positive peak of the frontal acceleration pattern offers a significantly lesser noisy source for identification of the heel-strike event. Determination of these event times facilitates the measurement of the temporal parameters (e.g., stance, swing, double support, step time, gait cycle time, etc.) and other relevant information associated with the spatial parameters (i.e. stride velocity, step length and stride length).

Gait speed (i.e., stride velocity) is computed (box 410 in FIG. 4) using information from the detected gait cycle and the amplitude of acceleration during the double support.

III. Detecting and Classifying the Lying Posture.

The system distinguishes lying from sitting and standing by comparing the angle of the vertical accelerometer signal $a_V(t)$ to that of the gravitational component. While the vertical accelerometer measures almost zero during lying periods, its value is significantly greater during sitting and upright postures—in some cases the value is close to the gravitational constant.

Figure 6:
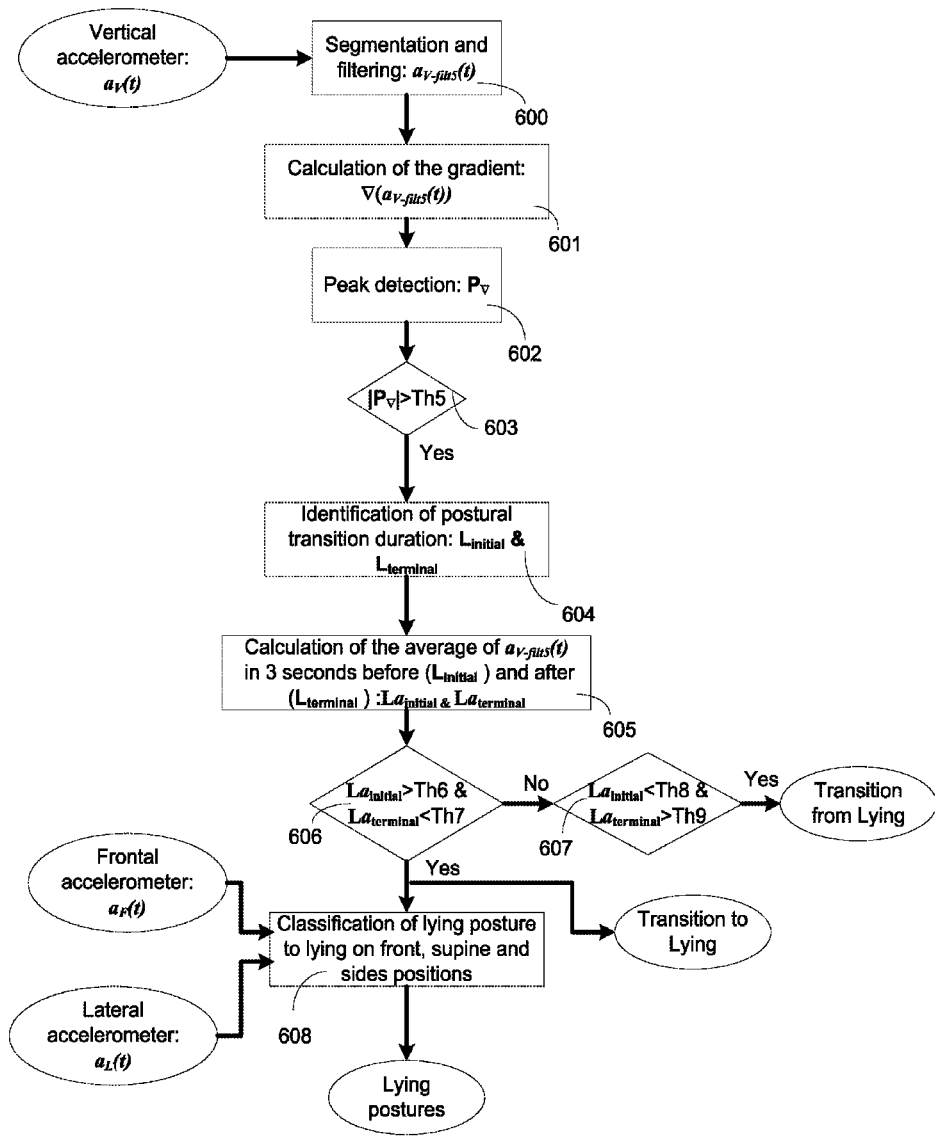
FIG. 6 is a flowchart of the algorithms used to detect and classify the lying posture.

The system identifies both the sit/stand-to-lying (SI/ST-L) and the mirror opposite (i.e., L-SI/ST) postural transitions using the following algorithm:
1) band-pass filter the vertical accelerometer signal (box 600 in FIG. 6);
2) calculate the gradient of the resulting the filtered signal $a_{V\text{-}filt5}(t)$ (box 601 in FIG. 6);
3) determine the maximum or minimum peak ($P_V$) of this gradient (box FIG. 6, box 602);
4) if the absolute value of the detected peak Pv exceeds a pre-defined threshold $Th_5$ (box 603, FIG. 6), estimate the duration of lying postural transition using a local peak detection scheme to identify peaks preceding ($L_{initial}$) and following ($L_{terminal}$) $P_V$ (box 604, FIG. 6);
5) identify a lying posture at the time of the detected peak when (i) the absolute value of the detected peak exceeds a threshold $Th_5$ (box 603, FIG. 6); and (ii) the average value of $a_{V\text{-}filt5}(t)$ during the 3 seconds preceding the $L_{initial}$ is i higher (iii) than a pre-defined threshold $Th_6$ (boxes 605-606, FIG. 6); and) the average value of $a_{V\text{-}filt5}(t)$ during the 3 seconds following the $L_{terminal}$ is lower than a threshold $Th_7$ (boxes 605-606, FIG. 6);
6) detect/identify a lying-to-sit/stand (L-SI/ST) postural transition at the time of the detected peak $P_V$ when (i) the absolute value of the detected peak exceeds a predefined threshold $Th_5$ (box 603, FIG. 6); and (ii) the average value of $a_{V\text{-}filt}(t)$ during the 3 seconds preceding the $L_{initial}$ is i lower than $Th_8$ (boxes 605-607, FIG. 6); and (iii) the average value of $a_{V\text{-}filt5}(t)$ during the 3 seconds following the $L_{terminal}$ is higher than a threshold $Th_9$ (boxes 605-607, FIG. 6);
7) classify the lying posture further as lying on back, lying on the front, or on the sides (left or right) on the basis of the value of the frontal accelerometer signal (box 608, FIG. 6);
8) further classify lying on the side into lying on the right and lying on the left according to the value of the lateral accelerometer signal.

Figure 7:
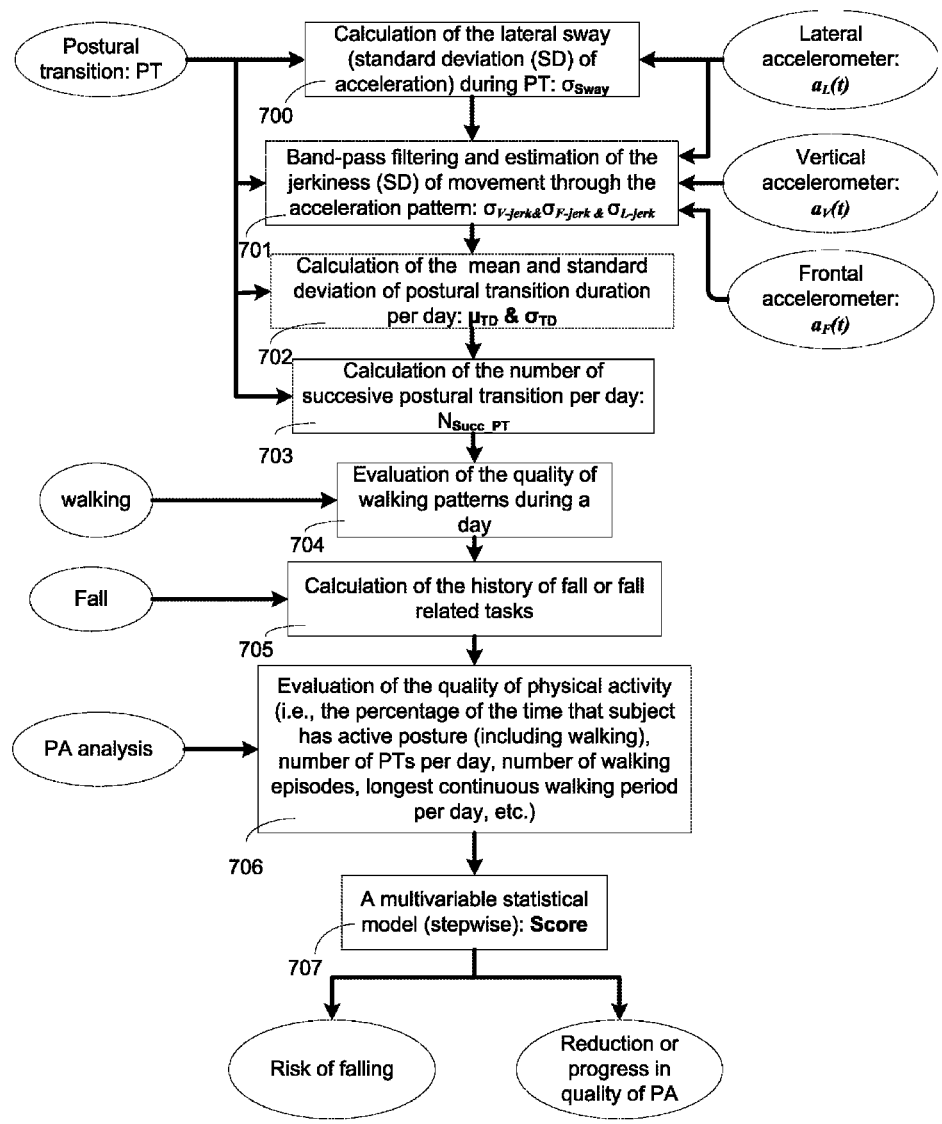
FIG. 7 is a flowchart of the algorithm used to compute the subject's risk of falling, and the quality of the subject's physical activity.

B. Computing the Risk of Falling and the Quality of the Subject's Physical Activity By monitoring the subject's physical activity, the invented system both evaluates the quality of the subject's physical activity, and computes the decline or progress in the subject's functional performance. FIG. 7 presents the flowchart of the corresponding software-based algorithm, developed as part of the invented system.

The subject's risk of falling (RoF) during everyday life is computed by first quantifying the quality of the subject's postural transitions. In turn, the quality of the postural transitions is quantified using the following algorithm:
1) estimate the lateral sway ($\sigma_{sway}$) of the subject during PT by computing the standard deviation of the lateral accelerometer during PT (box 700, FIG. 7);
2) estimate the jerkiness in the subject's movement in all directions ($\sigma_{V\text{-}jerk}$, $\sigma_{F\text{-}jerk}$, and $\sigma_{L\text{-}jerk}$)—computed as the standard deviation of the band-pass filtered acceleration signals in the frontal, vertical and lateral directions (box 701, FIG. 7);
3) compute the mean ($\mu_{TD}$) and standard deviation ($\sigma_{TD}$) of the durations of the subject's postural transitions ($\Delta T_2$), over a day (box 702, FIG. 7);
4) compute the number of successive postural transitions ($N_{Succ\_PT}$) required for a subject to accomplish a single task—an example is multiple unsuccessful attempts by a subject to rise from a chair (box 703, FIG. 7);
5) evaluate the quality of physical activity by computing the fraction of the time that subject has active posture (including walking); the number of PTs per day; the number of walking episodes during a day; and the longest continuous walking period per day (boxes 704-706, FIG. 7);
6) evaluate the subject's risk of falling by inputting the above parameters to a statistical model (e.g., stepwise) that provides a linear combination of the calculated parameters to yield a single score representative the subject's RoF (box 707, FIG. 7). A subject is considered to be at a high-risk of falling if the linear combination passes beyond a threshold, which may be predefined, or may change adaptively.

To identify a subject at a high risk of falling more accurately, the system continually adjusts the requisite threshold values based on the history of falls or other similar events detected by the algorithm (e.g., high-impact experienced shortly after a postural transition, very short ST-SI durations, etc.)

I. Automatic Fall Detection.

Figure 8:
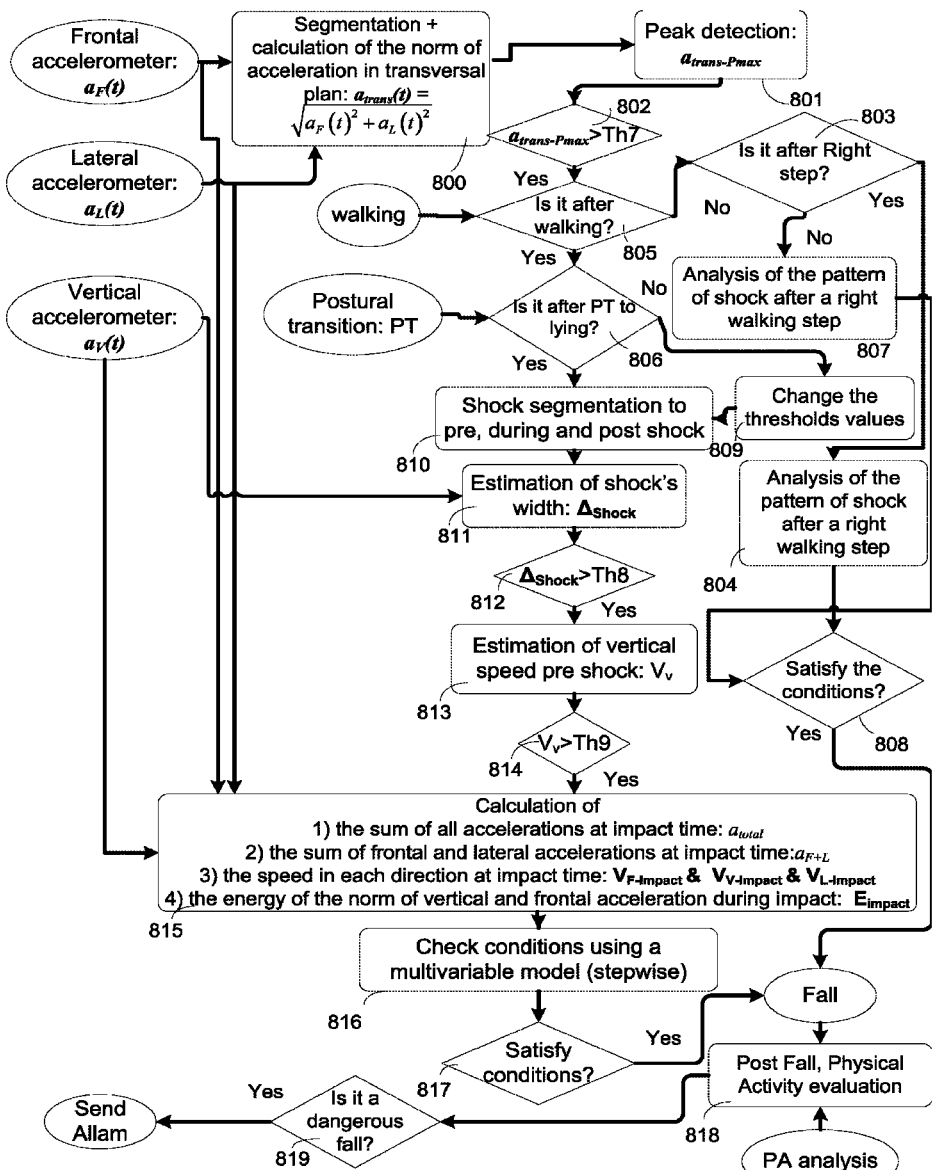
FIG. 8 is a flowchart of the algorithm used to automatically detect the subject's falls.

The present invention uses a novel algorithm, based solely on accelerometer signals, to automatically identify falls during the subject's everyday life with high sensitivity and specificity. The fall-detection algorithm described here uses information about the subject's physical activity, as well as posture. The flowchart in FIG. 8 describes in complete the algorithm developed to automatically detect the subject's falls. The following summarizes the algorithm:
1) compute the norm (magnitude) of acceleration in the transversal plane, $a_{trans}(t)$ from the frontal and lateral acceleration signals—$a_F(t)$ and $a_L(t)$, respectively—through:

$$a_{trans}(t) = \sqrt{[a_F(t)]^2 + [a_V(t)]^2} \text{ (box 800)};$$

2) apply a peak-detection algorithm (box 801) to atrans(t) to identify the presence of "shocks" $a_{trans\text{-}Pmax}$;

3) confirm a fall event by considering the subject's PA and posture prior to impact times (marked by the identified shocks)—this step is carried out using algorithms described above;
4) use different algorithms to identify a fall event, depending on the results of step (3) supra:
   (i) if impacts occur while subject is walking or turning, depending on whether the impacts occurred after right or left step, the algorithm chooses appropriate thresholds and coefficients required for subsequent steps ($Th_8$: box 812; $Th_9$: box 814; and coefficients of the multivariable model: box 816);
   (ii) if activity preceding the shock is not identified as walking, turning or any sequential locomotion (e.g., walking upstairs or downstairs,) the algorithm would identify as fall events only the shocks that occur after a postural transition to sitting or lying.
   (iii) Next, thresholds and coefficients required for subsequent steps are modified;
5) segment the shock-pattern following a postural transition into pre-shock, impact, and post-shock phases based on the location of local minimum peaks relative to the absolute maximum peak ($p_{max}$) in the signal $a_{trans}(t)$ (box 810, trans, FIG. 8); the set of thresholds chosen according to step (4) supra, and used by the algorithm depends on whether the post-shock posture is sitting or lying.
6) estimate the shock width ($\Delta_{shock}$) using the local minimum peaks before and after each the peak $p_{max}$ (box 811, FIG. 8); consider the peak to be an artifact and subsequently ignored if its width does not exceed the threshold $Th_8$ (box 812, FIG. 8);
7) if the peak is not an artifact, compute the subject's speed during the pre-shock phase by integrating the pattern of vertical accelerometer—$V_V(t)$ (box 813, FIG. 8); for the peak to be recognized as a fall, the peak of the velocity profile must exceed the threshold $Th_9$ (box 814, FIG. 8);
8) compute the following descriptors (box 815, FIG. 8):
   (i) sum of all accelerations at the time of impact $t_{impact}$ as:

$$a_{total}(t_{impact}) = a_F(t_{impact}) + a_V(t_{impact}) + a_V(t_{impact});$$

(ii) the sum frontal and lateral accelerations at impact time:

$$a_{F+L}(t_{impact}) = a_F(t_{impact}) + a_L(t_{impact});$$

(iii) the difference of speed in each direction at the impact time ($V_{F\text{-}impact}$, $V_{V\text{-}impact}$, and $V_{L\text{-}impact}$); and
   (iv) energy of the norm of vertical and frontal acceleration during the impact phase ($\Delta_{Shock}$):

$$E_{Impact} = \int_{\Delta Shock} \sqrt{a_F(t)^2 + a_V(t)^2} dt;$$

9) identify a fall event through a multivariable model (stepwise or linear combination) that uses the above descriptors as inputs and coefficients chosen in step (4) supra (box 816, FIG. 8);
10) identify a fall as "serious" if the post-fall activities represent an unusual activity pattern, such as a long-duration rest, or multiple unsuccessful postural transitions (boxes 818-819, FIG. 8); in one embodiment of the invention, an alarm will be set off following a "serious" fall;

II. Physical Activity Classification.

The algorithms described above will classify the subject's physical activity and posture, determine his or her risk of falling and quality of movements. In addition, several rules will be applied to improve the classifications performed by the above algorithms. These rules include, but are not limited to, the following:

1) If two contradictory states are detected (e.g., lying with walking or sitting with walking) preference is first given to lying, then to walking, and finally to postural transitions. This rule is based on the rationale that the lying posture is classified with the least amount of error. It should be noted that since the algorithms for different postural detections operate independently, two contradictory sets of activities may be identified.
2) Two successive postural transitions classified as the same type (e.g., SI-ST followed by SI-ST) are not possible—the classifications are modified according to the preceding and subsequent activities.
3) Elderly subjects cannot lean backwards after a SI-ST transition with a high likelihood. The algorithm estimates the trunk lean angle based on the trunk angle before ($\theta_{PT\text{-}pre}$) and/or following ($\theta_{PT\text{-}post}$) the postural transition.
   (i) Both $\theta_{PT\text{-}pre}$ and $\theta_{PT\text{-}post}$ are estimated based on the mean ($E[.]$) of the frontal acceleration during the rest period immediately before, or after a postural transition, according to the following formulas:

$$\theta_{PT\text{-}pre} = \sin^{-1}(E[a_F(t)|\text{pre-PT-rest}])$$

$$\theta_{PT\text{-}post} = \sin^{-1}(E[a_F(t)|\text{post-PT-rest}])$$

where $E[a_F(t)$ pre–PT–rest$]$ denotes the mean of the frontal acceleration signal during the rest period immediately before the postural transition; $E[aF(t)$ post–PT–rest$]$ denotes the corresponding mean after the postural transition.
   (ii) If the standard deviation of both frontal and vertical accelerations during a local interval before or after a postural transition were lower than a pre-defined threshold, the algorithm will classify that duration as a rest period.
   (iii) Sensor inclination ($\theta_{initial}$) is computed from the average of the frontal accelerometer signal during a recognized walking episode containing at least ten steps: $\theta_{initial} = \sin^{-1}(E[a_F(t)|\text{walking; 10 steps}])$.
   (iv) The backwards-leaning state is detected if, subtracting $\theta_{initial}$ from $\theta_{PT\text{-}pre}$ (or $\theta_{PT\text{-}post}$) yields a value lower than a pre-defined threshold.
4) The duration of the lying posture should be more than a specified length (e.g., 30 seconds).
5) For an episode to be classified as "walking," it must include at least three successive steps within a pre-defined interval.
6) Since it is improbable for a person, especially an elderly subject, to stand for long periods without any movements, long standing periods without additional activity (e.g., more than three minutes) are interpreted as sitting. This rule applies if the standard deviations of both the vertical and frontal accelerations are below pre-defined thresholds.

REFERENCES

[1] B. Najafi and K. Aminian, "Body movement monitoring system for elderly people, determines time and duration of postural transition (2000, European and US Patent)," EP1195139-A1 EP810920 5 Oct. 2000; US2004015103-A1 US398462 4 Apr. 2003, 2000.

[2] B. Najafi, K. Aminian, F. Loew, Y. Blanc, and P. A. Robert, "Measurement of stand-sit and sit-stand transitions using a miniature gyroscope and its application in fall risk evaluation in the elderly," *Ieee Transactions on Biomedical Engineering*, vol. 49, pp. 843-851, 2002.

[3] B. Najafi, K. Aminian, A. Paraschiv-Ionescu, F. Loew, C. J. Bula, and P. Robert, "Ambulatory system for human motion analysis using a kinematic sensor: Monitoring of daily physical activity in the elderly," *Ieee Transactions on Biomedical Engineering*, vol. 50, pp. 711-723, 2003.

[4] R. W. Bohannon, A. W. Andrews, and M. W. Thomas, "Walking speed: reference values and correlates for older adults," *J Orthop Sports Phys Ther*, vol. 24, pp. 86-90, 1996.

[5] K. Aminian, B. Najafi, C. Bula, P. F. Leyvraz, and P. Robert, "Spatio-temporal parameters of gait measured by an ambulatory system using miniature gyroscopes," *Journal of Biomechanics*, vol. 35, pp. 689-699, 2002.

[6] K. Aminian, B. Najafi, J. Gramiger, P. Morel, and N. Bijan, "Autonomous measuring unit for human movement has sensors, conditioning circuit, display, and circuit for recording kinematic parameters of body segment," ECOLE POLYTECHNIQUE FEDERALE LAUSANNE (ECOL-Non-standard) AMINIAN K (AMIN-Individual) BIJAN N (BIJA-Individual) GRAMIGER J (GRAM-Individual) MOREL P (MORE-Individual).

[7] K. Aminian, K. Rezakhanlou, E. De Andres, C. Fritsch, P. F. Leyvraz, and P. Robert, "Temporal feature estimation during walking using miniature accelerometers: an analysis of gait improvement after hip arthroplasty," *Medical & Biological Engineering & Computing*, vol. 37, pp. 686-691, 1999.

[8] S. R. Cummings, M. C. Nevitt, and S. Kidd, "Forgetting falls. The limited accuracy of recall of falls in the elderly," *J Am Geriatr Soc*, vol. 36, pp. 613-6, 1988.

[9] D. Oliver, M. Britton, P. Seed, F. C. Martin, and A. H. Hopper, "Development and evaluation of evidence based risk assessment tool (STRATIFY) to predict which elderly inpatients will fall: case-control and cohort studies," *Bmj*, vol. 315, pp. 104953, 1997.

[10] M. E. Tinetti, T. F. Williams, and R. Mayewski, "Fall risk index for elderly patients based on number of chronic disabilities," *Am J Med*, vol. 80, pp. 429-34, 1986.

[11] K. Doughty, R. Lewis, and A. McIntosh, "The design of a practical and reliable fall detector for community and institutional telecare," *J Telemed Telecare*, vol. 6 Suppl 1, pp. S150-4, 2000.

[12] U. Lindemann, A. Hock, M. Stuber, W. Keck, and C. Becker, "Evaluation of a fall detector based on accelerometers: a pilot study," *Med Biol Eng Comput*, vol. 43, pp. 548-51, 2005.

[13] Y. Depeursinge, J. Krauss, and M. El-Khoury, "Device for monitoring the activity of a person and/or detecting a fall, U.S. Pat. No. 6,201,476," 2001.

[14] N. Noury, G. Barralon, G. Virone, P. Boissy, M. Hamel, and P. Rumeau, "A smart sensor based on rules and its evaluation in daily routines," presented at 25th Annual International Conference of the IEEE Eng. Med. Biol. Society, 2003.

What is claimed is:

1. A body movement monitoring system comprising:
a data processing system comprising one or more processor circuits, said data processing system configured to process acceleration measurements generated by a sensor, the sensor adapted to be attached to an upper part of a body of a person and comprising at least one accelerometer component adapted to generate one or more acceleration signals in response to movement of the body, the data processing system programmed to:
    apply a filter to at least a portion of at least one of the one or more acceleration signals to obtain one or more filtered signals;
    determine an estimated postural transition duration for a postural transition based at least partly on one or more peaks in the one or more filtered signals;
    derive information related to the postural transition using the estimated postural transition duration, the information including at least one of: time of occurrence of the postural transition, duration of the postural transition, or type of the postural transition;
    apply a filter to a vertical accelerometer signal of the one or more acceleration signals for a time period corresponding to said duration of said postural transition, to obtain a filtered vertical acceleration signal;
    compute a gradient of the filtered vertical acceleration signal to obtain a gradient signal;
    identify a global extremum of said gradient signal;
    if the magnitude of the global extremum exceeds a threshold value, compare a first portion of the filtered vertical acceleration signal that precedes the global extremum to a second portion of the filtered vertical acceleration signal that is subsequent to the global extremum;
    if said comparison yields a first result, identify a lying posture; and
    if said comparison yields a second result, identify a transition from said lying posture.

2. The body movement monitoring system of claim 1, wherein said data processing system is further configured to determine a revised estimated postural transition duration that is more accurate than the estimated postural transition duration.

3. The body movement monitoring system of claim 2, wherein said data processing system is further programmed to derive at least part of the information by:
    estimating an inertial acceleration of the person during a time period corresponding to the revised estimated postural transition duration,
    said estimating comprising processing a frontal acceleration signal of the one or more acceleration signals to correct for a sagittal trunk tilt angle of the person during flail the time period corresponding to the revised estimated postural transition duration.

4. The body movement monitoring system of claim 2, wherein said data processing system is further programmed to derive at least part of the information by:
    estimating an inertial acceleration of the person during a time period corresponding to the revised estimated postural transition duration, said estimating comprising:
        applying one or more filters to a vertical acceleration signal of the one or more acceleration signals from the time period corresponding to the revised estimated postural transition duration to obtain one or more filtered versions of the vertical acceleration signal; and identifying one or more peaks in the one or more filtered versions of the vertical acceleration signal.

5. The body movement monitoring system of claim 2, wherein said data processing system is further programmed to derive at least part of the information by at least:
estimating an acceleration of the person during a time period corresponding to the revised estimated postural transition duration, said estimating comprising:
processing a frontal acceleration signal of the one or more acceleration signals to correct for a sagittal trunk tilt angle of the person during the time period corresponding to the revised estimated postural transition duration to obtain a corrected frontal acceleration signal;
using the corrected frontal acceleration signal and a vertical acceleration signal of the one or more acceleration signals, estimating time-varying inertial frontal and vertical acceleration signals;
removing a gravitational component from the estimated time-varying inertial vertical acceleration signal;
computing a time-varying magnitude signal corresponding to a square root of a sum of squares of said estimated time-varying inertial frontal and vertical acceleration signals;
applying at least one filter to said time-varying magnitude signal to obtain a filtered time-varying magnitude signal;
identifying a local extremum in said filtered time-varying magnitude signal preceding the time of occurrence of said postural transition (P_pre); and
identifying a local extremum in said filtered time-varying magnitude signal following the time of occurrence of said postural transition (P_post).

6. The body movement monitoring system of claim 5, wherein said data processing system is further programmed to perform at least one of:
classifying said postural transition as a transition to standing if P_pre is a local maximum and P_post is a local minimum; or
classifying said postural transition as a transition to sitting if P_pre is a local minimum and P_post is a local maximum.

7. The body movement monitoring system of claim 6, wherein said data processing system is further configured to reclassify said postural transition based on a classification of one or more postural transitions preceding or following said postural transition.

8. The body movement monitoring system of claim 1, wherein the postural transition is classified based on analysis of a positive extremum and a negative extremum of one or more identified peaks in one or more filtered versions of a vertical acceleration signal of the one or more acceleration signals.

9. The body movement monitoring system of claim 8, wherein the postural transition is classified as:
a postural transition to standing when the positive extremum is followed by the negative extremum, and
a postural transition to sitting when the negative extremum is followed by the positive extremum.

10. The body monitoring system of claim 9, wherein said data processing system is further configured to reclassify said postural transition based on the classification of one or more postural transitions preceding or following said postural transition.

11. The body movement monitoring system of claim 1, wherein said data processing system is further configured to:
identify a first local extremum which precedes said global extremum, wherein said first portion of the filtered vertical acceleration signal corresponds to a time period preceding the first local extremum;
identify a second local extremum which follows said global extremum, wherein said second portion of the filtered vertical acceleration signal corresponds to a time period following the second local extremum, wherein
the comparison yields the first result when (1) an average of said first portion of the filtered vertical signal exceeds a second threshold and (2) an average of said second portion of the filtered vertical signal is lower than a third threshold; and
the comparison yields the second result when (1) an average of said first portion of the filtered vertical signal is less than a fourth threshold and (2) an average of said second portion of the filtered vertical signal exceeds a fifth threshold.

12. The body movement monitoring system of claim 11, wherein said data processing system is further programmed to, if said comparison yields the first result, classify the lying posture as lying on back, lying on front, or lying on side, using a frontal accelerometer signal of said one or more acceleration signals.

13. The body movement monitoring system of claim 12, wherein said data processing system is programmed to distinguish a side on which the user lies, using a lateral accelerometer signal of said one or more acceleration signals.

14. The body movement monitoring system of claim 1, further including a wireless transmission system for wirelessly transmitting at least a portion of said one or more acceleration signals, at least a portion of the information derived by said data processing system, or both.

15. The body movement monitoring system of claim 1, wherein said at least one accelerometer component comprises a tri-axial accelerometer.

16. The body movement monitoring system of claim 1, wherein said at least one accelerometer component comprises a plurality of mono-axial accelerometers configured to measure accelerations in a plurality of perpendicular directions.

17. The body movement monitoring system of claim 1, further comprising one or more data storage systems configured to store said one or more acceleration signals, said derived information, or both.

18. The body movement monitoring system of claim 1, wherein said data processing system and said sensor reside in a sensing module that is supported by a patient during use.

19. The body movement monitoring system of claim 1, wherein said data processing system resides in a computer that is separate from the sensor.

20. The body movement monitoring system of claim 1, wherein said data processing system does not utilize gyroscope data in deriving the information related to the postural transition.

21. The body movement monitoring system of claim 1, wherein the information comprises time of occurrence of the postural transition.

22. The body movement monitoring system of claim 1, wherein the information comprises duration of the postural transition.

23. The body movement monitoring system of claim 1, wherein the information comprises type of the postural transition.

24. A method for monitoring body movement, the method comprising:
receiving acceleration measurements corresponding to one or more acceleration signals generated by at least one accelerometer component of a sensor unit attached to an upper part of a body of a person in response to movement of the body;

with a data processing system comprising one or more processor circuits:

applying a filter to at least a portion of at least one of the one or more acceleration signals to obtain one or more filtered signals;

determining an estimated postural transition duration for a postural transition based at least partly on one or more peaks in the one or more filtered signals;

deriving information related to the postural transition using the estimated postural transition duration, the information including at least one of: time of occurrence of the postural transition, duration of the postural transition, or type of the postural transition;

determining a revised estimated postural transition duration that is more accurate than the estimated postural transition duration; and deriving at least part of the information by estimating an acceleration of the person during a time period corresponding to the revised estimated postural transition duration, said estimating comprising:

processing a frontal acceleration signal of the one or more acceleration signals to correct for a sagittal trunk tilt angle of the person during the time period corresponding to the revised estimated postural transition duration to obtain a corrected frontal acceleration signal;

using the corrected frontal acceleration signal and a vertical acceleration signal of the one or more acceleration signals, estimating time-varying inertial frontal and vertical acceleration signals;

removing a gravitational component from the estimated time-varying inertial vertical acceleration signal;

computing a time-varying magnitude signal corresponding to a square root of a sum of squares of said estimated time-varying inertial frontal and vertical acceleration signals;

applying at least one filter to said time-varying magnitude signal to obtain a filtered time-varying magnitude signal;

identifying a local extremum in said filtered time-varying magnitude signal preceding the time of occurrence of said postural transition (P_pre); and identifying a local extremum in said filtered time-varying magnitude signal following the time of occurrence of said postural transition (P_post).

25. The method of claim 24, further comprising deriving, with the data processing system, at least part of the information by:

estimating an inertial acceleration of the person during a time period corresponding to the revised estimated postural transition duration, said estimating comprising processing a frontal acceleration signal of the one or more acceleration signals to correct for a sagittal trunk tilt angle of the person during a time period corresponding to the revised estimated postural transition duration.

26. The method of claim 24, further comprising deriving, with the data processing system, at least part of the information by:

estimating an inertial acceleration of the person during a time period corresponding to the revised estimated postural transition duration, said estimating comprising:

applying one or more filters to a vertical acceleration signal of the one or more acceleration signals from the time period corresponding to the revised estimated postural transition duration to obtain one or more filtered versions of the vertical acceleration signal; and identifying one or more peaks in the one or more filtered versions of the vertical acceleration signal.

27. Non-transitory computer storage that stores executable code that directs a computer system to at least:

apply a filter to at least a portion of at least one of one or more acceleration signals generated by at least one accelerometer component of a sensor unit attached to an upper part of a body of a person, the one or more acceleration signals generated in response to movement of the body;

determine an estimated postural transition duration for a postural transition based at least partly on one or more peaks in the at least a portion of the one or more acceleration signals that is filtered;

using the estimated postural transition duration, derive information related to the postural transition, the information including at least one of: time of occurrence of the postural transition, duration of the postural transition, or type of the postural transition;

apply a filter to a vertical accelerometer signal of the one or more acceleration signals for a time period corresponding to said duration of said postural transition, to obtain a filtered vertical acceleration signal;

compute a gradient of the filtered vertical acceleration signal to obtain a gradient signal;

identify a global extremum of said gradient signal;

if the magnitude of the global extremum exceeds a threshold value, compare a first portion of the filtered vertical acceleration signal that precedes the global extremum to a second portion of the filtered vertical acceleration signal that is subsequent to the global extremum;

if said comparison yields a first result, identify a lying posture; and if said comparison yields a second result, identify a transition from said lying posture.

\* \* \* \* \*